United States Patent [19]

Kisielowski et al.

[11] Patent Number: 4,697,035

[45] Date of Patent: Sep. 29, 1987

[54] PROCESS FOR THE PREPARATION OF BASICALLY SUBSTITUTED PHENYLACETONITRILES

[75] Inventors: Lothar Kisielowski; Ingomar Grafe; Walter Liebenow; Kurt H. Ahrens, all of Nuremberg, Fed. Rep. of Germany

[73] Assignee: Ludwig Heumann & Co., GmbH, Fed. Rep. of Germany

[21] Appl. No.: 740,250

[22] Filed: Jun. 3, 1985

[30] Foreign Application Priority Data

Jun. 15, 1984 [EP] European Pat. Off. ........ 84106868.7

[51] Int. Cl.$^4$ ........................................... C07C 121/78
[52] U.S. Cl. ................................... 558/344; 558/342; 558/390
[58] Field of Search ..................... 558/342, 344, 390

[56] References Cited

U.S. PATENT DOCUMENTS 3,261,859 7/1966 Dengel ............................... 558/390
4,350,636 9/1982 Kastner ........................... 558/390 X

FOREIGN PATENT DOCUMENTS 0047888 8/1981 Fed. Rep. of Germany .
1553708 12/1968 France .

OTHER PUBLICATIONS

The Chemistry of the Cyano Group, by Zvi Rappoport, 1970, p. 380.

Primary Examiner—Dolph H. Torrence
Attorney, Agent, or Firm—Ostrolenk, Faber, Gerb & Soffen

[57] ABSTRACT

A simplified process for the preparation of basically substituted phenylacetonitriles, in particular of verapamil, is described. This process is carried out with fewer stages and higher yields than the known processes according to the state of the art.

11 Claims, No Drawings

PROCESS FOR THE PREPARATION OF BASICALLY SUBSTITUTED PHENYLACETONITRILES

DESCRIPTION

This invention relates to a process for the preparation of basically substituted acetonitriles.

It is known that basically substituted phenyl acetonitriles have coronary vasodilator and antiarrhythmia properties and are therefore valuable medicaments for the treatment of various coronary diseases. The best known substance is α-isopropyl-α-[(N-methyl-N-homoveratryl)-γ-aminopropyl]-3, 4-dimethoxyphenylacetonitrile (verapamil, DE-PS No. 1 154 810).

Various processes for the preparation of such basically substituted phenylacetonitriles have been disclosed in DE-PS No. 1 154 810, DE-PS No. 1 158 083, DE-OS No. 2 059 923, DDR-PS No. 119 579 and DE-OS No. 3 121 766.

In the process described in DE-PS No. 1 154 810, the best known compound of this class of substances, verapamil, is prepared from α-isopropylveratryl cyanide corresponding to the formula

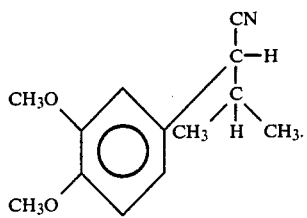

The starting material for this compound is 3,4-dimethoxybenzyl cyanide. According to Organikum, VEB Deutscher Verlag der Wissenschaften, Berlin 1976, pages 412 and 270, and DDR-PS No. 9451, this compound is prepared from veratrol and formaldehyde/aqueous HCl and reaction of the chloromethyl compound with NaCN. When the process described in the literature for the preparation of 3,4-dimethoxybenzyl cyanide was repeated, in no case could the yields indicated in the literature be obtained. Only small quantities of 3,4-dimethoxy-benzyl chloride were obtained, which did not enable α-isopropyl-veratryl cyanide to be prepared economically.

Moreover, these processes are not applicable on a technical scale since it is difficult to prepare the intermediate product corresponding to the formula:

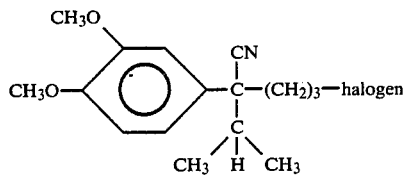

with sufficient purity and in high yields.

In DE-OS No. 2 263 527, there is described a process for the preparation of verapamil in which α-isopropylveratryl cyanide is reacted with 3-methyl-formamido-1-chloropropane to form 2-(3.4-dimethoxyphenyl)-2-isopropyl-5-methylformamidovaleronitrile, which is condensed with homoveratryl aldehyde after the formic acid group has been split off. This process also provides only low yields.

In DE-AS No. 2 631 222, there is described a process for the preparation of basically substituted phenylacetonitriles in which an α-isopropyl-benzyl cyanide is condensed with an ω-halogen acetal and the nitrile acetal obtained is then converted into the nitrile aldehyde by reaction with aqueous acid, and the nitrile aldehyde is then subjected to a hydrogenating condensation with an amine.

In all these processes, the preparation of the starting materials from which they are obtained involves difficulties so that the desired end product is only obtained in low yields.

It is an object of the present invention to provide a new and simplified process for the preparation of verapamil and related compounds.

This object is achieved according to the invention by a process for the preparation of basically substituted phenylacetonitriles corresponding to the general formula I

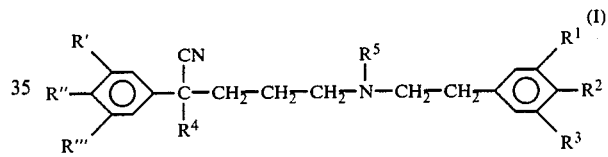

wherein R', R'', R''', $R^1$, $R^2$ and $R^3$ denote, independently of one another, a hydrogen atom, a halogen atom, a lower alkyl group, a lower alkoxy group, a lower alkylmercapto group or an amino group which is optionally mono- or disubstituted by a lower alkyl group; $R^4$ denotes a straight chained or branched aliphatic hydrocarbon group having 1 to 6 carbon atoms or a saturated or unsaturated cyclic hydrocarbon group having 5 or 6 carbon atoms and $R^5$ denotes a hydrogen atom or a lower alkyl group, characterised in that a compound corresponding to the general formula II

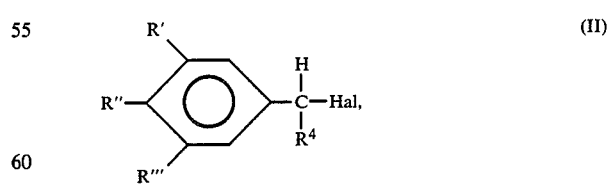

wherein R',R'',R''' and $R^4$ have the meanings indicated above and Hal stands for a halogen atom, is reacted with a cyanide of the formula Me—CN, wherein Me denotes a monovalent metal, to form the nitrile of formula III

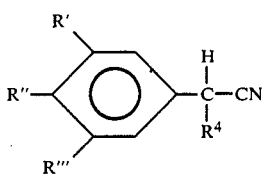

(III)

wherein R', R'', R''' and R⁴ have the meanings indicated above and the resulting compound III is reacted with a β-substituted propionitrile corresponding to the general formula IV

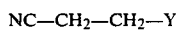

NC—CH₂—CH₂—Y (IV)

wherein Y denotes a lower alkoxy group or the group NH—Z wherein Z represents a lower alkyl group, a C₅-C₆-cycloalkyl group or an optionally substituted phenyl group, and the resulting compound V

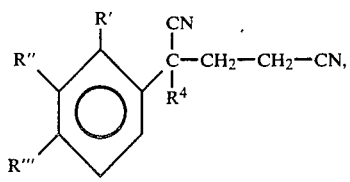

(V)

wherein R',R'',R''' and R⁴ have the meanings indicated above, is reduced in the presence of a phenylethylamine corresponding to formula VI

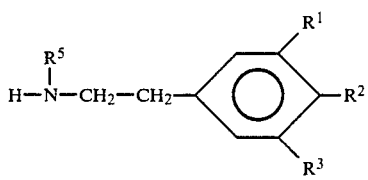

(VI)

wherein $R^1$, $R^2$, $R^3$ and $R^5$ have the meanings indicated above, and the substance obtained is optionally converted into a pharmacologically acceptable salt by reaction with a physiologically acceptable acid.

In the general formula I, R',R'',R''',$R^1$,$R^2$ and $R^3$ represent, independently of one another, a hydrogen atom, a halogen atom such as a fluorine, chlorine, bromine or iodine atom, a lower alkoxy group such as a butoxy, n- or i-propoxy, ethoxy or methoxy group, a lower alkyl mercapto group such as an ethyl- or methylmercapto group, or an amino group which may be mono- or disubstituted by a lower alkyl group. The term "lower alkyl group" is used here to denote an alkyl group having 1 to 4 carbon atoms. By "lower alkoxy group" is meant an alkoxy group having 1 to 4 carbon atoms in the alkyl moiety. $R^4$ denotes a straight chained or branched aliphatic hydrocarbon group having 1 to 6 carbon atoms, preferably a lower alkyl group, in particular a methyl group or a saturated or unsaturated cyclic hydrocarbon having 5 or 6 carbon atoms, for example a cyclopentyl or cyclohexyl group or a cyclopentenyl or cyclohexenyl group. $R^5$ denotes a hydrogen atom or a lower alkyl group such as a n- or i-butyl, n- or i-propyl, ethyl or methyl group, the latter being preferred. In the formula Me-CN denoting a metal cyanide used in the first stage, Me stands for a monovalent metal, for example potassium or sodium, the latter being preferred. In formula IV, Y stands for a lower alkoxy group as defined above or the group NH-Z wherein Z denotes a lower alkyl group, a C₅-C₆-cycloalkyl group or a substituted or unsubstituted phenyl group. The substituents optionally used on the phenyl group may be, for example, halogen atoms or lower alkyl groups.

In the first stage of the process according to the invention, the compound corresponding to formula II is reacted with the metal cyanide. Compound II may easily be prepared from the corresponding alcohol and the corresponding aqueous hydrohalic acid. The reaction is carried out at 10° to 40° C. and preferably using aqueous hydrochloric acid. Thus, for example, α-isopropyl-veratryl alcohol corresponding to the formula

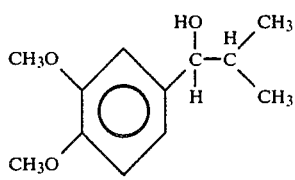

may be reacted with aqueous hydrochloric acid to form the corresponding compound II. Compound II is reacted with a metal cyanide, preferably sodium cyanide. in the presence of a phase transfer catalyst such as the cetyl trimethylammonium salt or tetrabutylammonium salt and 1 to 10% by weight of water to form the nitrile corresponding to formula III. The reaction is preferably carried out in an alkaline medium, preferably in an amine such as triethylamine, and at a temperature of 30° to 80° C. As already mentioned, the reaction is carried out in the presence of a phase transfer catalyst. The reaction under conditions of phase transfer is carried out by the general methods described in Synthesis, 1973, pages 441 and 447.

In the next stage of the process according to the invention, compound III obtained in the first stage is reacted with a β-substituted propionitrile corresponding to the general formula IV. The reaction is carried out in an inert solvent such as dimethylformamide and at a temperature of from 40° to 90° C. By this method, compound V may be obtained pure in a virtually quantitative yield.

In the third stage of the process according to the invention, the dinitrile compound of formula V is reduced in the presence of a phenyl ethylamine compound of formula VI. This reduction is preferably carried out as a catalytic hydrogenation using a noble metal catalyst, preferably Pd/C. In a preferred procedure for carrying out this stage, the dinitrile V is reacted with 0.9 to 1.5 equivalents, preferably 1.0 to 1.1 equivalents of the phenyl ethylamine compound of formula VI or a salt thereof and 1 to 10% by weight, based on the amine, of the Pd/C catalyst which contains 1 to 10% by weight of Pd, based on the quantity of C, and the reaction is carried out at temperatures from 30° to 80° C., preferably at 60° C., at normal pressure or under an excess pressure of up to 6 bar. The solvents used may be lower alcohols, acetic acid or aromatic hydrocarbons, preferably lower aliphatic alcohols such as ethanol. The reaction mixtures are worked up by conventional methods.

The resulting compound of formula I may, if required, be converted into a pharmacologically acceptable salt thereof.

Both inorganic and organic acids are suitable. Examples of inorganic acids include hydrochloric acid and hydrobromic acid. Oxalic acid is an example of a suitable organic acid. Any pharmacologically suitable inorganic or organic acids could in principle be used for conversion into a physiologically acceptable salt.

Compared with the known processes of the state of the art, the process according to the invention provides the advantages of a smaller number of stages, better partial and total yields and the use of milder and physiologically less harmful reagents.

The invention is illustrated by the Examples.

EXAMPLE 1

(a) Preparation of α-isopropylveratryl cyanide 457.4 g (2 mol) of α-isopropyl-veratryl chloride, 108 g (2.2 mol) of sodium cyanide, 10 mol-% of phase transfer catalyst, 100 ml of water and 800 ml of triethylamine are stirred together for 5 hours at 60° C. After the addition of 60 ml of 30% sodium hydroxide solution and 300 ml of water, the organic phase is separated off. After removal of the triethylamine by distillation, the residue is distilled in a fine vacuum. The distillate obtained is recrystallised from methanol/water.

Yield: 310 g=71% of the theoretical, melting range: 50° to 52° C.

(b) Preparation of 4-(3,4-dimethoxyphenyl)-4-cyano-5- methylcapronitrile 438.4 g (2 mol) of α-isopropyl-veratryl cyanide and 204.2 g (2.4 mol) of 3-methoxypropionitrile are dissolved in 400 ml of dimethylformamide, 36 ml of a 5.5 molar solution of sodium methylate are added, and the mixture is heated to 85° C. for 1/2 hour. After cooling, water is added to the reaction mixture and the reaction product separates by crystallisation. Recrystallised from methanol/water, the product melts at 97° C.

Yield: 506 g=92.9% of theoretical.

(c) Preparation of α-isopropyl-α-[(N-methyl-N-homoveratryl)aminopropyl]-3,4-dimethoxy-phenylacetonitrile 408 g (1.5 mol) of 4-(3 4-dimethoxyphenyl)-4-cyano-5-methylcapronitrile and 30 g of Pd/C, 5%, are suspended in 1700 ml of isopropanol in a hydrogenation apparatus and the whole apparatus is flushed with nitrogen. After the addition of 20 ml of Dehyquart A ®, a stream of hydrogen is passed through the apparatus with vigorous stirring and the receiver is filled with hydrogen. 325 g (1.66 mol) of N-methyl-homoveratrylamine are added to the reaction mixture, which is then hydrogenated ated at 50° to 60° C under a light excess hydrogen pressure. Hydrogenation is completed after 4 to 6 hours.

After removal of the catalyst, the isopropanol solution is concentrated by evaporation under vacuum. The residue is taken up in ethyl acetate. Isopropanolic HCl is added to the solution until the reaction is acid. The verapamil-HCl which crystallises out is suction filtered and recrystallised from isopropanol.

White crystals, melting range: 139.7° to 145° C.

EXAMPLE 2

Preparation of α-isopropyl-α-[(N-homoveratryl)-aminopropyl]-3,4-dimethoxyphenylacetonitrile 272 g (1.0 mol) of 4-(3, 4-dimethoxyphenyl)-4-cyano-5-methylcapronitrile and 15 g of Pd/C, 5%, are suspended in 1100 ml of isopropanol in a hydrogenation apparatus and the whole apparatus is flushed with nitrogen. 20 ml of Dehyquart A ® are added and a stream of hydrogen is passed through the apparatus with vigorous stirring and the receiver is filled with hydrogen. After the addition of 200 g (1.1 mol) of homoveratrylamine, hydrogenation is carried out under a light excess hydrogen pressure for 4 to 5 hours at 50° to 60° C.

After removal of the catalyst, the isopropanol solution is concentrated by evaporation under vacuum. The oily residue is taken up in 600 ml of methylene chloride and the solution is washed once with 600 ml of 2N HCl, then with 300 ml of water, and the solvent is drawn off under vacuum. The residue is dissolved in 800 ml of ethyl acetate in the heat. Norverapamil-HCl which crystallises out is suction filtered and recrystallised from isopropanol.

White crystals, melting point: 141.1° to 142.1° C., yield: 339 g=71%.

We claim:

1. Process for the preparation of basically substituted phenyl acetonitriles corresponding to the general formula I

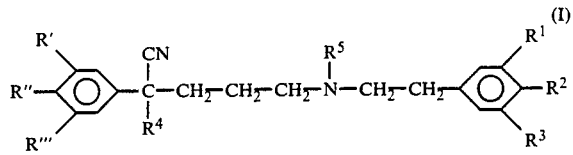

wherein R',R", R''', $R^1$, $R^2$ and $R^3$ denote, independently of one another, a hydrogen atom, a halogen atom. a lower alkyl group, a lower alkoxy group, a lower alkylmercapto group, an amino group or an amino group which is mono- or disubstituted by a lower alkyl group, $R^4$ denotes a straight chained or branched aliphatic hydrocarbon group having 1 to 6 carbon atoms or a saturated or unsaturated cyclic hydrocarbon group having 5 or 6 carbon atoms, and $R^5$ denotes a hydrogen atom or a lower alkyl group, characterised in that a compound corresponding to the general formula II

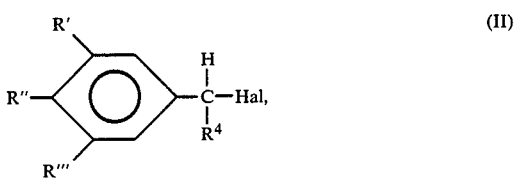

wherein R',R",R"' and R⁴ have the meanings indicated above and Hal stands for a halogen atom, is reacted with a cyanide of the formula Me—CN, wherein Me denotes a monovalent metal, to form the nitrile of formula III

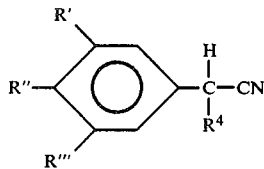 (III)

wherein R',R",R"' and R⁴ have the meanings indicated above, the resulting compound III is reacted with a β-substituted propionitrile corresponding to the general formula IV

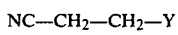 (IV)

NC—CH₂—CH₂—Y wherein Y denotes a lower alkoxy group or the group NH-Z, wherein Z represents a lower alkyl group, a C₅-C₆-cycloalkyl group or an optionally substituted phenyl group, and the resulting compound V

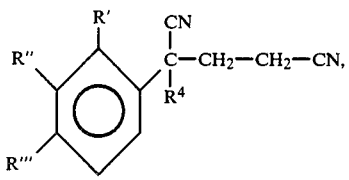 (V)

wherein R', R", R "' and R⁴ have the meanings indicated above, is reduced in the presence of a phenylethylamine corresponding to formula VI

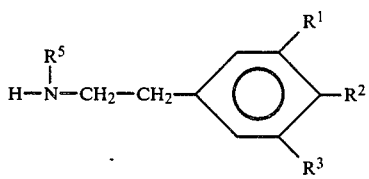 (VI)

wherein R¹, R², R³ and R⁵ have the meanings indicated above, or in the presence of a salt thereof.

2. Process according to claim 1, characterised in that a compound corresponding to the general formula I is prepared, in which R' denotes a hydrogen atom, R" and R"' denote each a methoxy group, R⁴ denotes an isopropyl group, R⁵ denotes a methyl group, R¹ denotes a hydrogen atom and R² and R³ denote each a methoxy group.

3. Process according to claim 1 or claim 2, characterised in that the reduction is carried out in the presence of a phenylethylamine of formula VI or a salt thereof and a noble metal catalyst, in a quantity of from 1 to 10% by weight, based on compound VI, the reaction being carried out at a temperature of 30° to 80° C. at normal pressure or under a hydrogen pressure of up to 6 bar.

4. Process according to one of the claims 1 or 2, characterised in that compound II is reacted with cyanide in an alkaline medium, and 1 to 10% of water, in the presence of a phase transfer catalyst.

5. Process according to claim 4, characterised in that the phase transfer catalyst used is a quaternary ammonium salt, in a quantity of 1 to 20 mol-%.

6. Process according to one of the claims 1 or 2, characterised in that compound III is reacted with 3-methoxypropionitrile in dimethylformamide with sodium alcoholate at a temperature of 40° to 90° C.

7. Process according to claim 1 or 2, characterized in that the compound of formula I is converted into a pharmacologically acceptable salt by reaction with a physiologically acceptable acid.

8. Process according to claim 3 characterized in that the nobel metal catalyst is palladium on carbon.

9. Process according to claim 4 in which the alkaline medium comprises triethylamine.

10. Process according to claim 5 characterized in that the quarternary ammonium salt is cetytrimethylammonium chloride.

11. Process according to claim 10 characterized in that compound II is reacted with cyanide in triethylamine and 1 to 10% of water in the presence of said phase transfer catalyst, and that the reduction is carried in the presence of phenylethylamine of formula VI or a salt thereof and a palladium catalyst in a quantity of from 1 to 10% by weight based on compound VI, the reaction being carried out at a temperature of 30° to 80° C. at a normal pressure or under a hydrogen pressure of up to 6 bar.

* * * * *